United States Patent [19]

Hillstead

[11] Patent Number: 5,116,365
[45] Date of Patent: May 26, 1992

[54] STENT APPARATUS AND METHOD FOR MAKING
[75] Inventor: Richard A. Hillstead, Miami, Fla.
[73] Assignee: Cordis Corporation, Miami Lakes, Fla.
[21] Appl. No.: 660,127
[22] Filed: Feb. 22, 1991
[51] Int. Cl.⁵ .............................................. A61F 2/06
[52] U.S. Cl. .......................................... 623/1; 623/12
[58] Field of Search .................. 623/1, 11, 12; 604/96

[56] References Cited
U.S. PATENT DOCUMENTS

| | | |
|---|---|---|
| 4,140,126 | 2/1979 | Choudhury . |
| 4,503,569 | 3/1985 | Dotter . |
| 4,733,665 | 3/1988 | Palmaz . |
| 4,856,516 | 8/1989 | Hillstead . |
| 4,878,906 | 11/1989 | Lindemann et al. ............ 623/1 |
| 4,954,126 | 9/1990 | Wallsten ..................... 623/1 |

Primary Examiner—David Isabella
Assistant Examiner—Debra S. Brittingham
Attorney, Agent, or Firm—Watts, Hoffmann, Fisher & Heinke

[57] ABSTRACT

A stent for reinforcing a vessel wall is disclosed. The stent is constructed from two elongated wires which are each bent into a series of tight bends. The two wires are permanently adhered at a first interconnection junction. The two wires are then wrapped around a mandrel repeatedly forming two opposing series of interconnections. The two wires are then permanently adhered at a second interconnection junction after a desired stent length is obtained. The completed stent forms a cylindrical form which can be expanded from an initial diameter to a larger implanted diameter by application of a radially outward force from a balloon catheter or the like.

18 Claims, 4 Drawing Sheets

STENT APPARATUS AND METHOD FOR MAKING

TECHNICAL FIELD

The present invention relates to an endoprosthesis device for implantation within a body vessel, typically a blood vessel.

BACKGROUND ART

A type of endoprosthesis device, commonly referred to as a stent, is placed or implanted within a blood vessel for treating stenoses, strictures, or aneurysms in the blood vessel. These devices are implanted within the vascular system to reinforce collapsing, partially occluded, weakened, or abnormally dilated sections of the blood vessel. Stents also have been successfully implanted in the urinary tract or the bileducts to reinforce those body vessels.

One common procedure for implanting the endoprosthesis or stent is to first open the region of the vessel with a balloon catheter and then place the stent in a position that bridges the weakened portion of the vessel.

Prior art patents refer to the construction and design of both the stent as well as the apparatus for positioning the stent within the vessel. One representative patent is U.S. Pat. No. 4,140,126 to Chaudhury which issued Feb. 20, 1979. This patent discloses a technique for positioning an elongated cylindrical stent at a region of an aneurysm to avoid catastrophic failure of the blood vessel wall. The stent disclosed in the '126 patent was a cylindrical shape that expands to its implanted configuration after insertion with the said of a catheter.

A second prior art patent to Dotter, U.S. Pat. No. 4,503,569 which issued Mar. 12, 1985 discloses a spring stent which expands to an implanted configuration with a change in temperature. The spring stent is implanted in a coiled orientation and heated to cause the spring to expand.

U.S. Pat. No. 4,733,665 to Palmaz which issued Mar. 29, 1988 discloses a number of stent configurations for implantation with the said of a catheter. The catheter includes a mechanism for mounting and retaining the vascular prosthesis or stent, preferably on an inflatable portion of the catheter. The stent is implanted by positioning it within the blood vessel and monitoring its position on a viewing monitor. Once the stent is properly positioned, the catheter is expanded and the stent separated from the catheter body. The catheter can then be withdrawn from the subject, leaving the stent in place within the blood vessel.

U.S. Pat. No. 4,856,516 to Hillstead entitled "Endovascular Stent Apparatus and Method" discloses a radially expandable stent for placement within a subject vessel. The stent is constructed from an elongated wire that is bent into a series of tight bends which are wrapped around a mandrel to form a series of loops. These loops are then interconnected by half hitch junctions. The disclosure of the '516 patent to Hillstead is incorporated herein by reference.

U.S. patent application Ser. No. 240,000 entitled "Radially Expandable Endoprosthesis and the Like" discloses a generally cylindrical stent formed from a wire that is bent into a series of tight bends and then spirally wound about a cylindrical mandrel to form the stent. If a radially outward force is applied to the stent the sharp bends in the wire tend to straighten and the stent diameter enlarges. One technique for implanting this stent uses a deflated balloon catheter to position the stent within a vessel. Once the stent is properly positioned the balloon is inflated to press the stent against the inner wall linings of the vessel. The balloon is then deflated and withdrawn from the vessel, leaving the stent in place.

DISCLOSURE OF THE INVENTION

The present invention concerns a stent for placement within a subject. A stent built according to the present invention uses one or more elongated flexible filaments that are repeatedly wrapped around a mandrel and interconnected along two, substantially parallel sets of junctions separated by the mandrel.

A feature of the stent allows for the omission of one or more stent segments thereby creating gaps to accommodate branching or crossing vessels within the subject vessel.

The completed stent is of a sturdy, yet flexible nature. It is capable of being easily placed within a subject vessel in a reduced diameter configuration that fits within a guide catheter. When properly positioned, the stent can be expanded using a balloon catheter. The implanted stent provides support and reinforcement to the subject vessel as it heals.

These and other objects of the invention will be better understood from the following description of the invention which is described in conjunction with the accompanying drawings.

DETAILED DESCRIPTION

Figure 1:
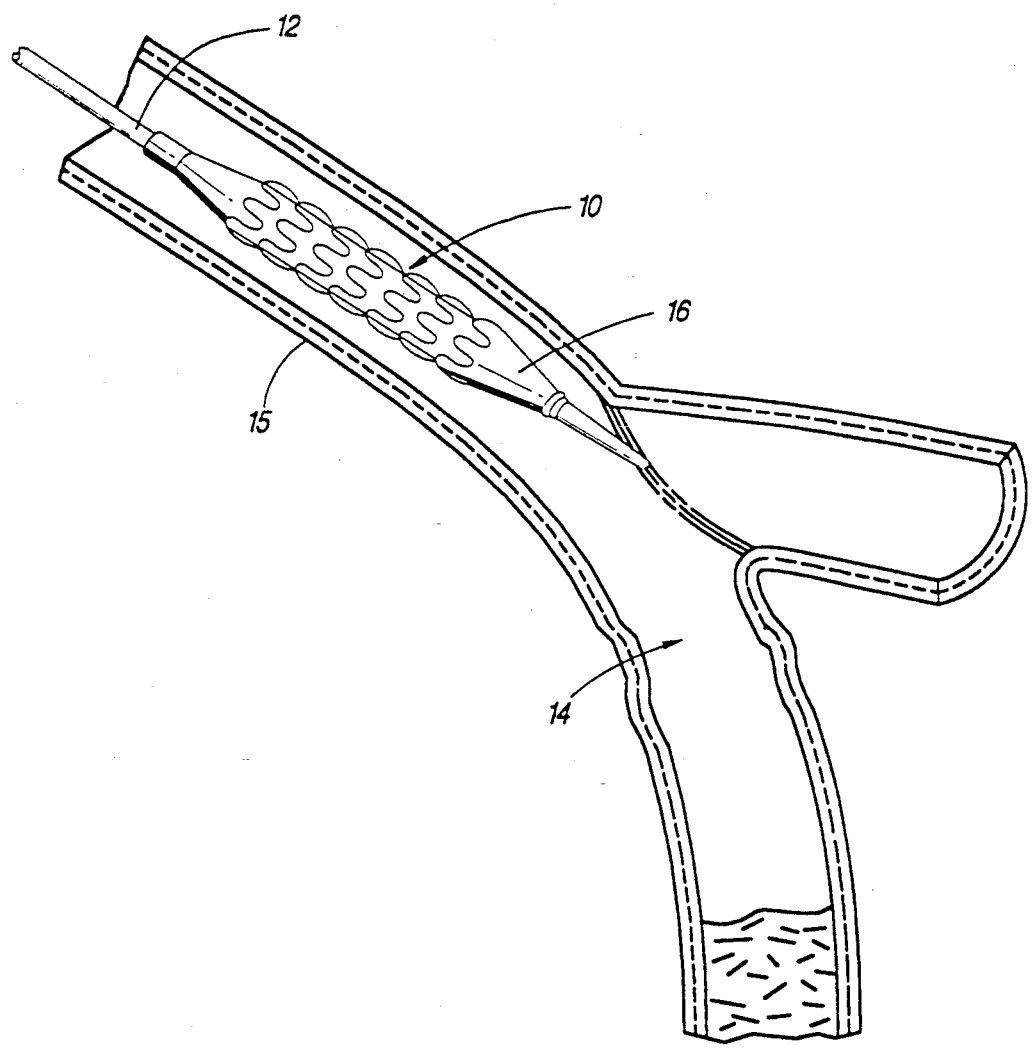
FIG. 1 is a schematic depiction of a stent carried by a balloon catheter as the stent is routed to an implantation position.
Figure 2:
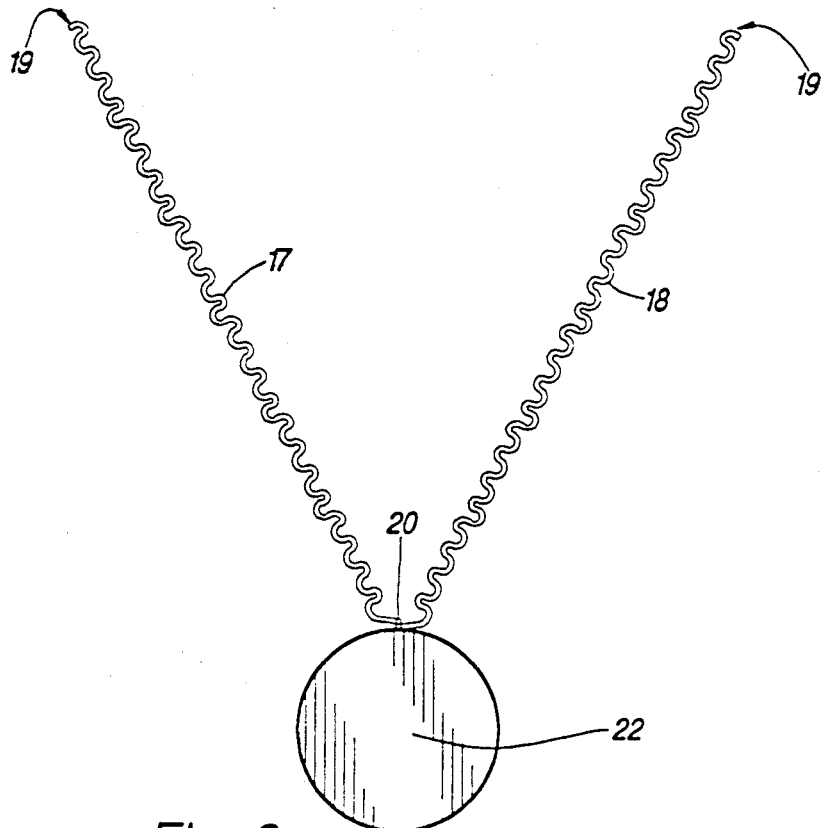
FIG. 2 is an end elevation view showing a cylindrical mandrel used in fabricating the stent from two wire filaments.

Turning now to the drawings, FIG. 1 shows a generally cylindrical stent 10 mounted to a balloon catheter 12 which is being routed through a patient's cardiovascular system to a weakened region 14 of a blood vessel 15. The balloon catheter 12 is of a conventional design and includes a catheter portion that defines a passageway extending from the catheter's proximal to distal end. The passageway allows fluid to be routed to a balloon 16 near the catheter's distal tip to inflate the balloon. As the balloon inflates it exerts a radially outward force against the stent 10 causing the stent to expand into contact with an inner wall of the blood vessel 15.

To release the stent within the blood vessel 15, the balloon 16 is then deflated causing the balloon and stent to separate. The stent 10 is then fixed within the blood vessel 15 due to frictional engagement between the stent and the inner wall lining of the blood vessel 15. The deflated balloon 16 can then be freely withdrawn from the stent. As this procedure is being accomplished, the attending physician can monitor progress of the stent implantation on a viewing monitor to determine the adequacy of the placement.

FIGS. 2-5 illustrate a stent constructed using two elongated filaments 17, 18, typically wires. Each filament 17, 18 forms a series of bends 19. The filaments 17, 18 are permanently adhered together at a first interlocking junction 20 located at a first end 21 (FIG. 4) of the stent 10. The two filaments are then repeatedly wrapped around respective semicylinder surfaces of cylindrical mandrel 22. The filaments 17, 18 are interconnected together by twisting a portion of each together along two, substantially aligned series of junctions 24, 25 on opposite sides of the mandrel 22.

Once the filaments 17, 18 are interlinked to achieve a desired length stent, the two filaments are permanently adhered together at a second interlocking junction 28 located at a second end portion 30 of the stent 10.

The interlocking junctions 20, 28 can be adhered together by welding, soldering, suturing or tying. In the situation where the junctions are tied or sutured, the material used for the tying or suturing could be bio-degradable and in fact such material would be preferred.

In accordance with an alternate construction, a single filament forms the stent 10. In this construction, the junction 20 is formed by bending a wire in the approximate shape of the wires 17, 18 and wrapping the wire halves along the semicylindrical mandrel surfaces.

A feature of the stent 10 constructed in accordance with the present invention is its ability to expand as outward pressure is applied to its length by the balloon 16. This ability stems from a combination of the factors as previously discussed above. The main factor, however, is the series of sharp bends 18 applied to the filaments 17, 18 from which the stent 10 is constructed.

An additional feature of the proposed construction is the omission of segments along length portions of the stent 10. This construction would accommodate for example, the use of the stent wherein side or branch vessels are encountered and would allow unimpeded fluid flow to those side or branching vessels through judicious placement of the stent.

Figure 3:
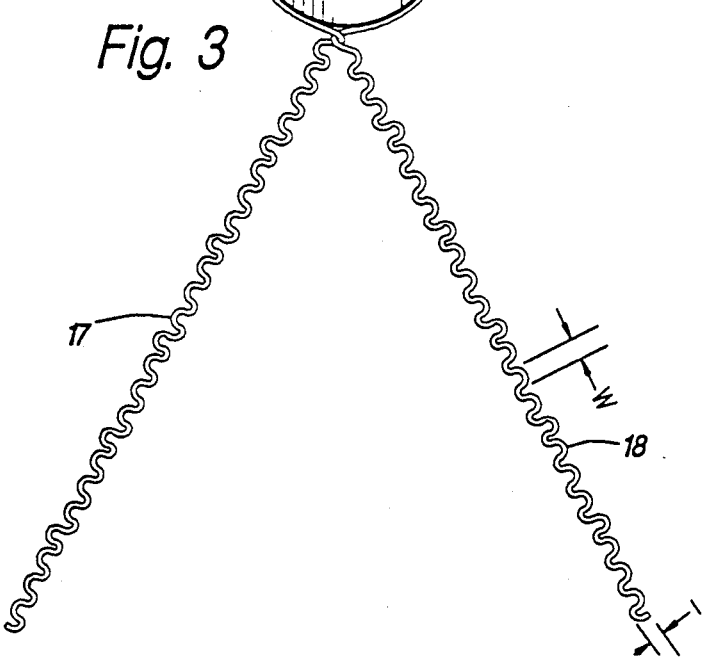
FIG. 3 is an end elevation view of the mandrel supporting a partially constructed stent.
Figure 4:
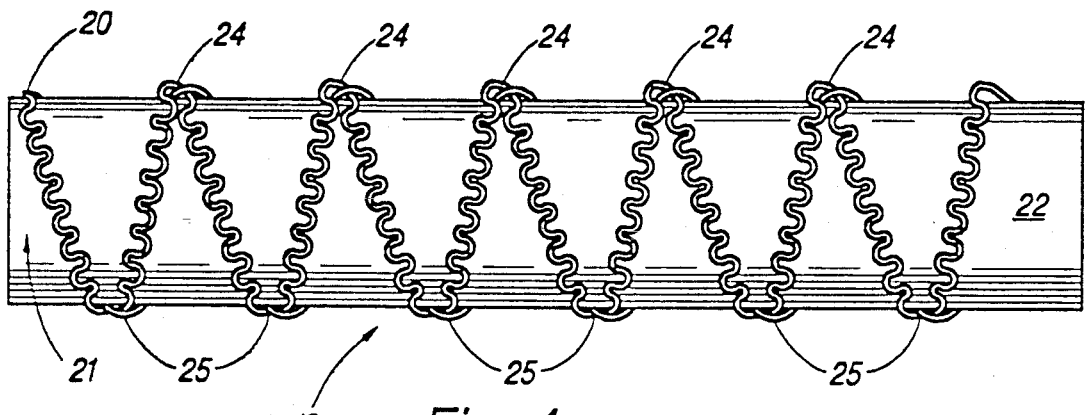
FIG. 4 is a side elevation view of the mandrel shown in FIGS. 2 and 3 supporting a stent constructed in accordance with the invention.
Figure 5:
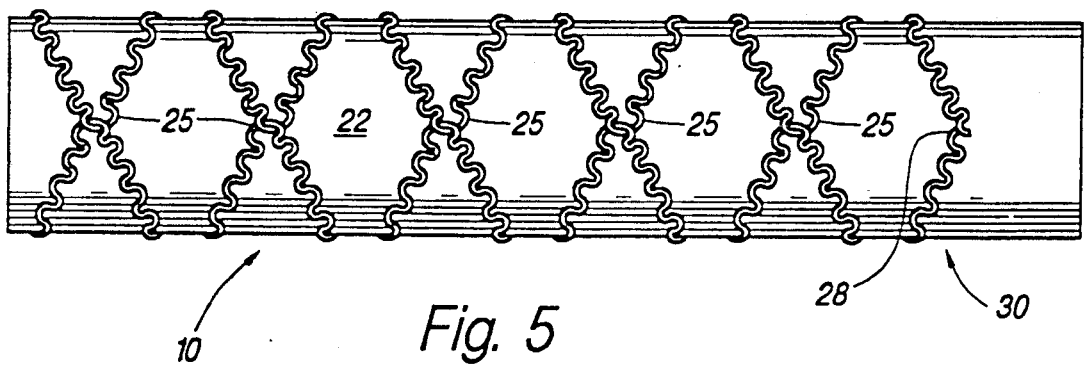
FIG. 5 is a side elevation view of the FIG. 4 mandrel rotated 90 degrees about a mandrel center axis.

A preferred stent 10 is constructed using tantalum wire having a diameter of 5 thousandths of an inch. Before they are straightened by the balloon 16, the bends have typical widths w of 0.048±0.002 inch and lengths 1 of 0.042±0.003 inch (FIG. 3).

Figure 6:
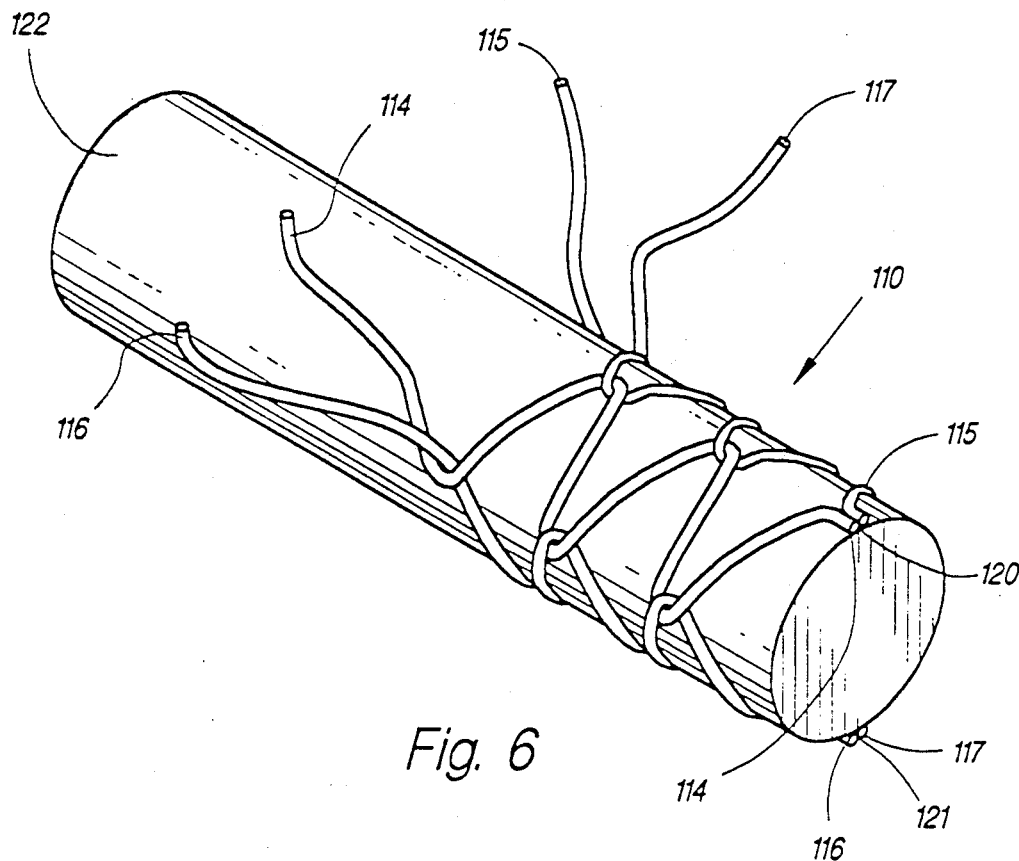
FIG. 6 is a perspective view of a mandrel depicting an alternate filament interconnection scheme for constructing a stent; and, FIG. 7 is a side elevation view of the completed alternate embodiment of a stent constructed using the FIG. 6 interconnection scheme.
Figure 7:
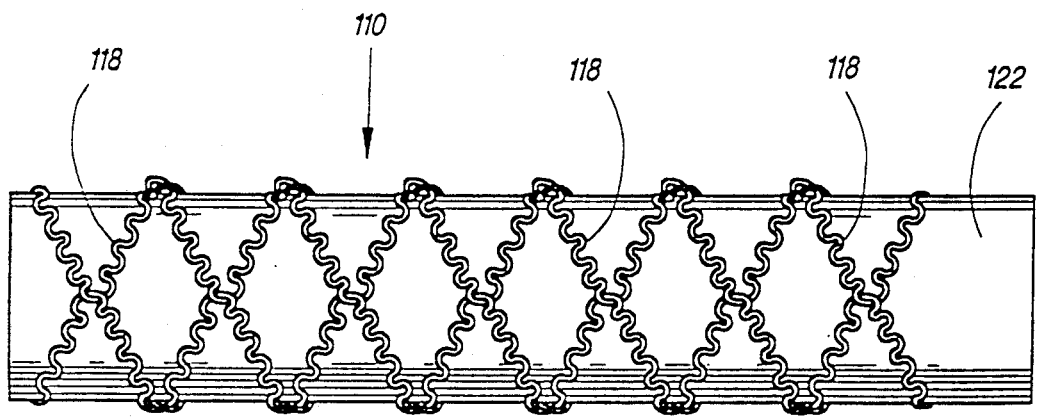

FIGS. 6 and 7 illustrate an alternate embodiment of a stent 110 using four filaments 114, 115, 116 and 117. The filaments are paired together on sides of a mandrel 122. Each pair is permanently adhered at junctions 120, 121. The filaments are then taken in opposite directions until they meet a filament from the opposite pair. Filaments 114 and 116 are then intertwined as are filaments 115, 117. The filaments then reverse directions and proceed towards the other filament in its pair. Filaments 114 and 115 are then intertwined as are filaments 116, 117. The filaments then proceed back in opposite directions engaging a quarter segment of the cylindrical mandrel and repeat the process until a desired stent length is obtained. The pairs of filaments 114, 115 and 116, 117 are then permanently adhered at ending junctions (not shown). FIG. 7 illustrates the completed stent 110 supported by the mandrel 122.

FIG. 6 illustrates the filaments without any bends in order to clarify the stent's structure. However, as illustrated in FIG. 7, the stent 110 does have bends 118. The junctions 120, 121 and the ending junctions can be formed by soldering, welding, tying or suturing. If tied or sutured, a bio-degradable material for the tying or suturing is preferred.

The stent has been described with a degree of particularity. It is the intent that the invention include all alterations from this embodiment falling within the spirit or scope of the appended claims.

I claim:

1. A stent for use within a subject vessel comprising a cylindrical support defining a fluid flow through passage, said support dimensioned to fit within an interior of said vessel and having opposite first and second end portions, said support characterized by:
   a) said support being constructed from at least one elongated flexible filament defining a plurality of relatively tightly spaced bends;
   b) said filament being interlocked together at a first interlocking junction located at said first end portion of said cylindrical support;
   c) said filament being intertwined together at a first set of junctions substantially aligned along a portion of said stent;
   d) said filament being intertwined together at a second set of junctions substantially aligned along an opposite portion of said stent; and,
   e) said filament being permanently adhered together at a second interlocking junction at said second end portion of said cylindrical support.

2. The stent of claim 1 wherein said support comprises two elongated filaments, said filaments being permanently adhered at said first and second interlocking junctions.

3. The stent of claim 1 wherein gaps are left along a length portion of said stent to accommodate branches in the vessel so that said stent does not block off fluid flow through said branch.

4. The stent of claim 1 wherein said stent is radially expandable from a first outer diameter which fits within said vessel to a second increased diameter which contacts an inner wall surface of said vessel to reinforce said inner wall.

5. The stent of claim 1 wherein an inner diameter of said stent is adapted to frictionally engage a non-inflated balloon catheter and be carried by said non-inflated catheter into a blood vessel.

6. A stent for use within a subject vessel comprising a cylindrical support defining a fluid flow through passage, said support dimensioned to fit within an interior of said vessel and having opposite first and second end portions, said support characterized by:
   a) said support being constructed from two elongated flexible filaments, each filament defining a plurality of series of relatively tightly spaced bends;
   b) said filaments being permanently adhered together at a first interlocking junction located at said first end portion of said cylindrical support;
   c) said filaments being interconnected together at a first set of junctions substantially aligned along a portion of said stent;
   d) said filaments being interconnected together at a second set of junctions substantially aligned along an opposite portion of said stent;

e) said filaments being permanently adhered together at a second interlocking junction at said second end portion of said cylindrical support;

wherein said first stent is radially expandable from a first outer diameter which fits within said vessel to a second increased diameter which contacts an inner wall surface of said vessel to reinforce said inner wall, sand wherein an inner diameter of said stent is adapted to frictionally engage a non-inflated balloon catheter and be carried by said non-inflated catheter into a blood vessel.

7. The stent of claim 6 wherein gaps are left along a length portion of said stent to accommodate branches in the vessel so that said stent does not block off fluid flow through said branches.

8. A cylindrically shaped support for use in a subject vessel comprising a flexible elongated filament bent at a midpoint to define two filament portions that diverge in two directions away from one end of the support along curved segments to define a cylindrical form wherein said curved segments extend along areas that meet at a sequence of junctions along the length of the cylindrical form, overlap other segments and are reoriented to traverse a given section of the cylindrical form; said curved segments meeting at a second end of the support.

9. The support of claim 8 wherein each curved segment bounds a semi-cylindrical section of the cylinder.

10. The support of claim 8 comprising two filaments each bent at a midpoint to form end positions on opposite sections at one end of the cylindrical form and each curved segment traverses one quadrant of said cylinder.

11. A stent for use within a subject vessel comprising a cylindrical support defining a fluid flow through passage, said support dimensioned to fit within an interior of said vessel and having opposite first and second end portions, said support characterized by:
 a) said support being constructed from at least one elongated flexible filament, said filament defining a plurality of series of relatively tightly spaced bends;
 said support being interlocked together at a first interlocking junction located at said first end portion of said cylindrical support;
 c) said support being intertwined together at a first set of junctions substantially aligned along a portion of said stent;
 d) said support being intertwined together at a second set of junctions substantially aligned along an opposite portion of said stent; and,
 e) said support being permanently adhered together via welding at a second interlocking junction at said second end portion of said cylindrical support.

12. A stent for use within a subject vessel comprising a cylindrical support defining a fluid flow through passage, said support dimensioned to fit within an interior of said vessel and having opposite first and second end portions, said support characterized by:
 a) said support being constructed from at least one elongated flexible filament, said filament defining a plurality of series of relatively tightly spaced bends;
 b) said support being interlocked together at a first interlocking junction located at said first end portion of said cylindrical support;
 c) said support being intertwined together at a first set of junctions substantially aligned along a portion of said stent;
 d) said support being intertwined together at a second set of junctions substantially aligned along an opposite portion of said stent; and,
 e) said support being permanently adhered together via soldering at a second interlocking junction at said second end portion of said cylindrical support.

13. A stent for use within a subject vessel comprising a cylindrical support defining a fluid flow through passage, said support dimensioned to fit within an interior of said vessel and having opposite first and second end portions, said support characterized by:
 a) said support being constructed from at least one elongated flexible filament, said filament defining a plurality of series of relatively tightly spaced bends;
 b) said support being interlocked together at a first interlocking junction located at said first end portion of said cylindrical support;
 c) said support being intertwined together at a first set of junctions substantially aligned along a portion of said stent;
 d) said support being intertwined together at a second set of junctions substantially aligned along an opposite portion of said stent; and,
 e) support being permanently adhered together via tying or suturing at a second interlocking junction at said second end portion of said cylindrical support.

14. The stent of claim 13 wherein the material used for the tying or suturing is bio-degradable.

15. A stent for sue within a subject vessel comprising:
 a) a cylindrical support defining a fluid flow through passage, said support dimensioned to fit within an interior of said vessel;
 b) said support being constructed from two elongated flexible filaments, each filament defining a plurality of series of relatively tightly spaced bends;
 c) said filaments being permanently adhered together at a first interlocking junction located at said first end portion of said cylindrical support;
 d) said filaments being interconnected together at a first set of junctions substantially aligned along a portion of said stent;
 e) said filaments being interconnected together at a second set of junctions substantially aligned along an opposite portion of said stent;
 f) said filaments being permanently adhered together via welding at a second interlocking junction at said second end portion of said cylindrical support;

wherein said stent is radially expandable from a first outer diameter which fits within said vessel to a second increased diameter which contacts an inner wall surface of said vessel to reinforce said inner wall, and wherein an inner diameter of said stent is adapted to frictionally engage a non-inflated balloon catheter and be carried by said non-inflated catheter into a blood vessel.

16. A stent for use within a subject vessel comprising:
 a) a cylindrical support defining a fluid flow through passage, said support dimensioned to fit within an interior of said vessel;
 b) said support being constructed from two elongated flexible filaments, each filament defining a plurality of series of relatively tightly spaced bends;

c) said filaments being permanently adhered together at a first interlocking junction located at said first end portion of said cylindrical support;
d) said filaments being interconnected together at a first set of junctions substantially aligned along a portion of said stent;
e) said filaments being interconnected together at a second set of junctions substantially aligned along an opposite portion of said stent;
f) said filaments being permanently adhered together via soldering at a second interlocking junction at said second end portion of said cylindrical support;

wherein said stent is radially expandable from a first outer diameter which fits within said vessel to a second increased diameter which contacts an inner wall surface of said vessel to reinforce said inner wall, and wherein an inner diameter of said stent is adapted to frictional engage a non-inflated balloon catheter and be carried by said non-inflated catheter into a blood vessel.

17. A stent for use within a subject vessel comprising:
a) a cylindrical support defining a fluid flow through passage, said support dimensioned to fit within an interior of said vessel;
b) said support being constructed from two elongated flexible filaments, each filament defining a plurality of series of relatively tightly spaced bends;
c) said filaments being permanently adhered together at a first interlocking junction located at said first end portion of said cylindrical support;
d) said filaments being interconnected together at a first set of junctions substantially aligned along a portion of said stent;
e) said filaments being interconnected together at a second set of junctions substantially aligned along an opposite portion of said stent;
f) said filaments being permanently adhered together via typing or suturing at a second interlocking junction at said second end portion of said cylindrical support;

wherein said stent is radially expandable from a first outer diameter which fits within said vessel to a second increased diameter which contacts an inner wall surface of said vessel to reinforce said inner wall, and wherein an inner diameter of said stent is adapted to frictionally engage a non-inflated balloon catheter and be carried by said non-inflated catheter into a blood vessel.

18. The stent of claim 17 wherein the material used for the tying or suturing is bio-degradable.

* * * * *